(12) United States Patent
Koizumi et al.

(10) Patent No.: US 7,244,838 B2
(45) Date of Patent: Jul. 17, 2007

(54) **METHOD FOR DETECTING, IDENTIFYING AND COUNTING *VIBRIO PARAHAEMOLYTICUS* USING GENE (RPOD) SEQUENCE ENCODING RNA POLYMERASE σ70 FACTOR**

(75) Inventors: Takeshi Koizumi, Chiba (JP); Satoshi Yamamoto, Chiba (JP); Takeshi Itoh, Tokyo (JP); Hiroshi Nakagawa, Tokyo (JP)

(73) Assignee: Nichirei Corporation, Tokyo (JP)

( * ) Notice: Subject to any disclaimer, the term of this patent is extended or adjusted under 35 U.S.C. 154(b) by 524 days.

(21) Appl. No.: 10/485,362

(22) PCT Filed: Aug. 1, 2002

(86) PCT No.: PCT/JP02/07842

§ 371 (c)(1),
(2), (4) Date: Jan. 30, 2004

(87) PCT Pub. No.: WO03/014393

PCT Pub. Date: Feb. 20, 2003

(65) Prior Publication Data

US 2004/0265822 A1  Dec. 30, 2004

(30) Foreign Application Priority Data

Aug. 3, 2001  (JP) ............................. 2001-235806

(51) Int. Cl.
| | | |
|---|---|---|
| C07H 21/04 | (2006.01) | |
| C07H 21/02 | (2006.01) | |
| C12Q 1/00 | (2006.01) | |
| C12Q 1/68 | (2006.01) | |
| C12P 19/34 | (2006.01) | |

(52) U.S. Cl. .............................. 536/23.7; 435/4; 435/6; 435/91.2; 536/23.1; 536/24.2; 536/24.3; 536/24.32; 536/24.33

(58) Field of Classification Search ................. 435/4, 435/6, 91.2; 536/23.1, 23.7, 24.2, 24.3, 24.32, 536/24.33
See application file for complete search history.

(56) References Cited

FOREIGN PATENT DOCUMENTS

| | | | |
|---|---|---|---|
| EP | 0 556 504 A2 | 8/1993 | |
| EP | 0 965 636 A1 | 12/1999 | |
| JP | 4-293486 | 10/1992 | |
| JP | 08-256798 | 10/1996 | |

OTHER PUBLICATIONS

Mastumoto, Chiho et al., "Pandemic spread of an O3:K6 clone of *Vibrio parahaemolyticus* and Emergence of Related Strains Evidenced by Arbitrarily Primed PCR and toxRS Sequence Analyses," *Journal of Clinical Microbiology*, vol. 28, No. 2, Feb. 2000, 578-585.

Yung Bu Kim et al., "Identification of *Vibrio parahaemolyticus* Strains at the Species Level by PCR Targeted to the toxR Gene," *Journal of Clinical Microbiology*, vol. 37, No. 2, Apr. 1999, 1173-1177.

Yamamoto, Satoshi, et al., "Phylogeny of the genus Pseudomonas: intrageneric structure reconstructed from the nucleotide sequences of gyrB and rpoD genes," *Microbiology*, vol. 146, No. 10, Oct. 2000, 2385-2394.

Chiayin Lee and Shwu-Fen Pan, Rapid and specific detection of the thermostable direct . . . , Journal of General Microbiology, vol. 139, p. 3225-3231 (1993).

Satoshi Yamamoto and Shigeaki Harayama, Phylogenetic relationships of *Pseudomonas putida*. . . , International Journal of Systematic Bacteriology, vol. 48, p. 813-819 (1998).

*Primary Examiner*—Rodney P Swartz
(74) *Attorney, Agent, or Firm*—Sughrue Mion, PLLC

(57) ABSTRACT

To prepare high-performance specific gene-amplification primers for detecting, quantitatively determining or identifying *Vibrio parahaeinolyticus* having low possibility of mis-identification and practically sufficient amplification efficiency and amplification specificity.

We have determined the nucleotide sequences of rpoD genes encoding RNA polymerase σ70 factor of type strains of the genus *Vibrio* and of stock strains of *Vibrio parahaemolyticus* (strains containing and those not containing toxin gene); elucidated the phylogenetic relation, and identified nucleotides which are characteristic in *Vibrio parahaemolyticus*, thereby enabling the design of probes containing them and having high specificity, and primers for gene amplification having high specificity and excellent amplification efficiency.

17 Claims, 3 Drawing Sheets

FIG. 3

```
V.p-ConsensusSeq     1 ACTCGCRAAGGCGAAATCGACATCGCAAAACGCATTGAAGAAGGTATTAACCAAGTTCAA   60
C123-ConsensusSeq    1 ......G.............................T.......................   60
                       ****** ***************************** ***********************

V.p-ConsensusSeq    61 TCGTCTGTTGCTGAATACCCTGGCACTATTCCTTACATCCTAGAGCAATTTGATAARGTT  120
C123-ConsensusSeq   61 ...................W..Y..D..Y..R.....Y..T.....R.....Y....W  120
                       *******************  ** ** ** ** ***** ** ***** ***** *****

V.p-ConsensusSeq   121 CAGGCAGAAGARCTTCGTCTGACTGATTTAATCTCTGGCTTTGTAGATCCTGACGCTGAC  180
C123-ConsensusSeq  121 ..A..W.....AY.D.....W..W..CC.W..Y..W..H.....H..Y..W..Y..H..Y  180
                       ** ** ******* * ***** ** ** * ** ** ** ***** ** ** ** ** **

V.p-ConsensusSeq   181 GATACAGCWGCGCCAACCGCGACTCACATCGGTTCTGARCTGTCTGAARCTCAATTAGAA  240
C123-ConsensusSeq  181 ..Y..VR....H..R..R..R..R.....Y..........RA.....T....GY.....  240
                       ** ** **** ** ** ** ** ** ***** ************ ***** **** *****

V.p-ConsensusSeq   241 GAGGAAGACGAAGAAGACCTAGAAGATGATGAAGARAGCGATGACGATTCAGATGAYTCR  300
C123-ConsensusSeq  241 ..W.....Y..W......G.T..T..M..C.....WR.Y..Y..YRRYKMW.....HD.W  300
                       ** ***** ** ****** * ** ** ** ***** * ** ** *****      ***** *

V.p-ConsensusSeq   301 GAAGAAGATGTAGGTATTGAYCCAGAGCTRGCGCTTGAGAAATTCAACCAGCTACGCAGC  360
C123-ConsensusSeq  301 ..R........W.....Y.....W..RY.D.....W................R........Y  360
                       ** ********* ***** ***** *  ***** **************** ********

V.p-ConsensusSeq   361 ACATACCAAAATCTTCAGCTAGCGATCAATGAGTACGGCTACGACAGCCCGAAAGCAACC  420
C123-ConsensusSeq  361 ..V..Y.....Y.....RY.W..A.....C..RY....Y..YR.V..Y..K.....R..M  420
                       ** ** ***** *****  * ** ***** **  **** ** ** ** ***** **

V.p-ConsensusSeq   421 GTTGCTAACGAAATGATGCTRGACGTATTCAAAGAATTCCGTCTAACACCAAAACAGTTC  480
C123-ConsensusSeq  421 ..W..W..Y..RW.......A........YMRM..R..Y.....R..R..W........Y  480
                       ** ** ** **  *******  ********          ** ** ***** ** ********

V.p-ConsensusSeq   481 GACCACCTAGTGAACGAACTTCGYACWGCAATGGATCGCGTTCGTACTCAAGAACGTTTG  540
C123-ConsensusSeq  481 ..Y...Y....R..Y....Y.R.....NK.D.........Y.........W.....R..YY..  540
                       ** *** **** ** *** * ***** *  ********* ******** ******* ** **

V.p-ConsensusSeq   541 ATCATGAAGTCTGTGGTTGAATACGGCAAAATGCCGAAGAAATCGTTYATTGCCCTATTC  600
C123-ConsensusSeq  541 ........RK.WRYN.........................R.....Y..R..G..Y  600
                       ********  *  ****************************** ***** ** ** **

V.p-ConsensusSeq   601 ACTGGTAACGAATCAAGTGATGCATGGCTAGACGAGATCCTMGCATCTGACAAGCCATAC  660
C123-ConsensusSeq  601 ..W..Y..Y.....W.SH..W..W...Y.R..T..RR.YY.WK.W..W..Y.........  660
                       ** ** ** ***** *  ** ** ** * ** ** * ** * ** ** *********

V.p-ConsensusSeq   661 GCTGAGAAAATCAAACGTAACGAAGAAGAGATCCGTCGTTCAATCKCKAAGTTAAAAATG  720
C123-ConsensusSeq  661 .....R...R..Y........R.........R..Y..Y..Y.....R.T..RC....R...  720
                       ***** ** ** ******* *********** ** ** ** ***** * ** **** ***

V.p-ConsensusSeq   721 ATTGAAGAAGAGACATMTCTAAACGTACARAACATTAAAGACATCAGCCGTCGCATGTCT  780
C123-ConsensusSeq  721 .....RR.H..R..Y.....R.MM..W........Y..................Y....M.  780
                       *****  *  ** *****  *  ** ********* **************** **** *

V.p-ConsensusSeq   781 ATCGGTGAAGCGAAAGCACGCCGTGCG                                  807
C123-ConsensusSeq  781 ..........R....MK..Y.....K                                   807
                       ********** **** ** *****
```

METHOD FOR DETECTING, IDENTIFYING AND COUNTING *VIBRIO PARAHAEMOLYTICUS* USING GENE (RPOD) SEQUENCE ENCODING RNA POLYMERASE σ70 FACTOR

DETAILED DESCRIPTION OF THE INVENTION

1. Field of the Invention

The present invention relates to the field of identifying and testing microorganisms and pathogenic microbes using genes, and particularly, testing *Vibrio parahaemolyticus*. The present invention relates to a method for rapidly identifying and testing *Vibrio parahaemolyticus* that causes food poisoning in the summer season, so that the field of the present invention includes food processing, public health and clinical laboratory testing.

2. Background Art

At the site of food hygiene control, *Vibrio parahaemolyticus* is currently tested based on biochemical phenotypes. According to the inspection guidelines for food hygiene, test samples are inoculated and cultured on TCBS agar media so as to obtain the thus formed greenish blue putatively positive colonies which are unable to degrade saccharose, and then various tests to identify the biochemical properties are conducted on the greenish blue colonies for determination. However, there are many problems in conducting the tests to identify the biochemical properties at the site of food manufacturing control, because the tests require accomplished techniques and a great deal of time and labor. In order to correct the defects of the standard tests to identify the biochemical properties, development of a test method using genes has been attempted for the purpose of detecting and identifying *Vibrio parahaemolyticus* accurately, rapidly and simply.

DISCLOSURE OF INVENTION

The following test methods using genes for testing *Vibrio parahaemolyticus* have been developed so far, but they involve various problems.

For example, PCR primers have been developed for detecting *Vibrio parahaemolyticus* using as a target gyrB gene which encodes DNA gyrase β subunit (Japanese Patent Application Laying-Open (Kokai) No. 09-252783, Applied and Environmental Microbiology, Vol. 64, No. 2, P. 681-687). However, the primers are prepared by assuming sections of sequences which are different between *Vibrio parahaemolyticus* strain ATCC 17802 and *Vibrio alginolyticus* strain ATCC17749 as specific, as a result of sequence analysis conducted on the gyrB gene of each single strain. In other words, the primers have not been prepared based on the understanding of the phylogenetic relation of the genus *Vibrio* based on the gyrB gene sequence, so that the range of specificity is unclear. Also reported is a detection method which uses a PCR method using as a target toxR gene that has been found as a gene controlling a toxin gene of *Vibrio cholera* and known to be present also in *Vibrio parahaemolyticus* (Journal of Clinical Microbiology. 1999 Vol. 37 No. 4, p1173-1177). However, similar to the above detection primers using gyrB gene, PCR primers of this example are prepared by comparing the gene sequences of each strain of *Vibrio parahaemolyticus* and *Vibrio cholera*, which are relatively distant from each other among phyla, and then assuming as *Vibrio parahaemolyticus*-specific sequences, sections of the nucleotide sequences that are different between the two strains. Hence, these primers have also not been prepared based on the understanding of the phylogenetic relation based on the toxR gene sequence, so that the range of specificity is unclear. On the other hand, there is another detection method noticing a toxin gene of *Vibrio parahaemolyticus* (Japanese Patent Application Laying Open (Kokai) No. 4-293486). It is long known that *Vibrio parahaemolyticus* is divided into a type having a toxin (Thermostable direct haemolysin: TDH) which causes hemolysis by boring holes on the membranes of red blood cells (referred to as Kanagawa phenomenon), and a type having no such toxin. In addition to TDH, a recently found toxin is TRH (TDH related haemolysin: TRH) which is very similar to TDH and causes no Kanagawa phenomenon but causes diarrhea (1988: Infect Immun. Vol. 56, 961-965). PCR primers have been developed for specifically detecting tdh and trh genes encoding each toxin that is thought to cause the pathogenicity of *Vibrio parahaemolyticus* (Japanese Patent Application Laying Open (Kokai) No. 4-293486). However, not all constituents of *Vibrio parahaemolyticus* possess such a toxin gene. Most constituents of *Vibrio parahaemolyticus* derived from environment actually possess no such toxin gene. Since the total cell count of all constituents of *Vibrio parahaemolyticus* including strains that possess no toxin gene is considered important at the site of food hygiene control, the inspection guidelines for food hygiene require testing *Vibrio parahaemolyticus* regardless of the presence or absence of toxin. Accordingly, detection methods for a toxin gene, which notice toxin-production ability only, have no compatibility with standard methods which are based on biochemical examination, so that such detection methods are inappropriate as a detection and identification method at the site of food hygiene control. As described above, the practical use of currently available primers for detecting and identifying *Vibrio parahaemolyticus* is insufficient.

In addition to these detection methods, there have been reported methods for detecting a 0.76 Kb DNA fragment (Appl. Environ. Microbiol. 61(4):1311-1317) with unknown functions that is specifically present in *Vibrio parahaemolyticus* or hemolytic factors, such as tlh (Thermolabile haemolysin: Lett Appl Microbiol 1999, Vol. 28, 66-70) and σ-VPH (FEMS Microbiol Lett 1990; 55(3):339-45). However, none of these methods have been proved to be able to reliably detect *Vibrio parahaemolyticus*, and none of them can be actually used at the site of evaluation.

As described above, none of the genetic testing methods considers that bacterial "species" is a population containing genetic diversity, and a nucleotide sequence of a strain assumed to be a member of a certain bacterial population is used as a common sequence or a representative sequence of the population for designing PCR primers. However, gene mutation, which is rapidly accumulated by molecular evolution, particularly neutral mutation, being taken into consideration, a strain originally to be detected cannot always be detected because amplification may be inhibited if slight mutation in primer region decreased applicability as a primer. Moreover, it is feared that there may be misidentification, because the lack of consideration on differences with closely related species by phylogenetic analysis inhibits design of a primer having sufficient amplification specificity, such that an closely related strain that is not originally a target is detected.

Thus, the preparation of high-performance, specific gene-amplification primers for detecting, identifying and quantitatively determining *Vibrio parahaemolyticus* having a proven background for specificity, low possibility of misidentification, and practically sufficient amplification efficiency and specificity has been required.

To establish a method for specifically detecting a gene of a certain phylogenetic group of bacteria, it is required to collect and compare as many as possible nucleotide sequences of an organism group to be detected, and of an organism group which is phylogenetically close to the group. In addition, a gene targeted for specific detection is required to have a sufficiently different nucleotide sequence to enable discrimination from the closest relatives. Thus, a target gene must have a sufficiently rapid rate of evolution.

Further, a gene which is present independently from phylogeny, such as a toxin gene of *Vibrio parahaemolyticus*, that is spread horizontally at a high frequency, cannot be used. A σ70 factor encoded by rpoD gene that is used as a target in the present invention is a factor controlling gene expression in bacteria at the logarithmic phase, and is a protein essential for survival. Therefore the factor is appropriate for phylogenetic analysis of bacteria, because it is rarely spread horizontally and has an appropriate rate of evolution (Int. J. Syst. Bacteriol. 1998; 48, 813-819, Int. J. Syst. Bacteriol. 1999; 49, 87-95).

BRIEF DESCRIPTION OF DRAWINGS

FIG. 3 Information on specificities among the phyla of the nucleotide sequences (SEQ ID NOS 1 and 2, respectively in order of appearance) of rpoD gene of the genus Vibrio.

Figure 1:
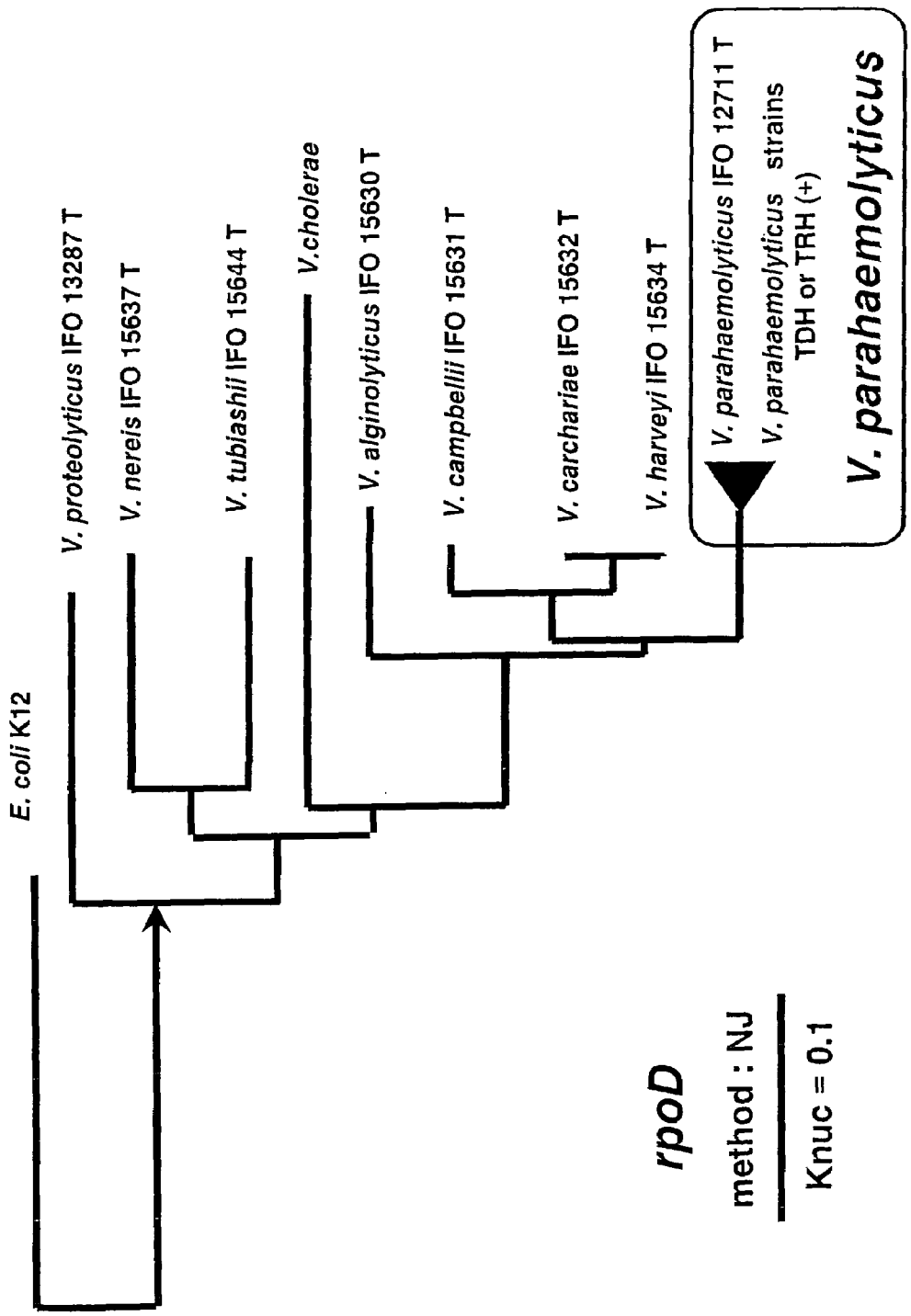
FIG. 1. Phylogenetic tree of the genus *Vibrio* based on rpoD gene sequence

The figure shows results after determination of the consensus sequences of the phyla V. p and C-1 to 3 (shown in FIG. 1), followed by homology analysis.

The upper case is V. p (the phylum that *Vibrio parahaemolyticus* belongs to); the lower case is the consensus sequence of the phyla C1 to 3. A section indicated by small sequential * denotes that it is the same sequence as the above sequence. A section indicated by large • denotes that it is a nucleotide specific to *Vibrio parahaemolyticus*. Symbols indicated are D=A or G or T; H=A or C or T; V=A or C or G; R=A or G; Y=C or T, K=G or T, M=A or C, S=G or C, W=A or T, and N=A or G or T or C.

Best Mode for Carrying out the Invention

We have already developed a simple method for determining nucleotide sequences of rpoD gene which encodes RNA polymerase σ70 factor by a PCR direct sequencing method (Japanese Patent Application Laying Open (Kokai) No. 8-256798). (Table 1)

Therefore, using the method, we have determined the nucleotide sequences of rpoD gene of the type strains of the genus *Vibrio* (purchased from Institute for Fermentation, Osaka (IFO)) and *Vibrio parahaemolyticus* stock strains (strains containing and those not containing toxin gene) as shown in Table 1 above, thereby clarifying the phylogenetic relation. Specifically, test strains shown in Table 1 were cultured for growth on brainlheart infusion media (NISSUI PHARMACEUTICAL Co., Ltd) supplemented with 2% NaCl at 35° C. overnight. Chromosome DNA was extracted from 1 ml of the culture solution using PUREGENE DNA Isolation Kit (Gentra SYSTEMS). Using the extracted DNAs as templates and rpoD amplification universal primers (s70S: ACgACTgACCCggTACgCATgTAYATg-MgNgARATgggNACNgT (SEQ ID NO: 9) and s70R:ATA-gAAATAACCAgACgTAAgTTNgCYTCNACCATYTCY TTYTT (SEQ ID NO: 11) described in Japanese Patent Application Laying Open (Kokai) No. 8-256798), an rpoD gene fragment of approximately 800 bp (positions: 334-1125 on rpoD gene sequence of *Eseherichia coli* strain K-12, corresponding to a region of positions 112 to 376 of an amino acid sequence) was amplified by a PCR method. Amplification reaction was performed using thermostable DNA polymerase (AmpliTaq Gold: Applied Biosystems) and a GENE MATE thermal cycler (ISC BioExpress). 50 µl of a reaction solution was prepared to contain 1 µg of DNA, 50 mM KCl, 10 mM Tris-HCl (pH 8.3), 1.5 mM MgC$_2$ 0.0 1% gelatin, 0.2 mM of each dNTP, 2.5U AmpliTaq Gold and 1 µM of each primer. The reaction condition consisting of activation (95° C. for 10 mm) with AmpliTaq Gold, 40 cycles of reaction (94° C. for 1 mm, 56° C. for 1 mm and 72° C. for 1 mm), and then elongation reaction (72° C. for 10 mm) was preformed. The resulting PCR products were subjected to 1% agarose gel (Sea Plaque GTG agarose: BioWhittaker Molecular Applications) electrophoresis (0.5× TAE, 100V for 30 mm), and then stained with ethidium bromide for 10 mm. The presence of the product was confirmed under ultraviolet radiation, excised from the gel, and then purified using Wizard PCR Preps DNA Purification System (Promega), thereby preparing a template for sequence reaction. Sequence reaction was performed using sequences for sequence reaction (s70 sS: ACgACTgAC-CCggTACgCATgTA (SEQ ID NO: 10) and s70sR:ATA-gAAATAACCAgACgTAAgTT (SEQ ID NO: 12) described in Japanese Patent Application Laying Open (Kokai) No. 8-256798) previously added to the above universal primers for rpoD gene as primers, ABI PRISM BigDye Terminator Cycle Sequencing Ready Reaction Kit (Applied Biosystems) and GENE MATE thermal cycler (ISC BioExpress). The reaction solution was prepared to have a final volume of 20 µl by mixing 20 ng of DNA, 3.2 pmol of primers and 8 µl of BigDye Terminator Ready Reaction Mix. The cycle sequence reaction consisting of heating at 92° C. for 10 min, and 25 cycles of 96° C. for 10 sec, 58° C. or 46° C. (corresponding respectively to s70sS:ACgACTgACCCgg-TACgCATgTA (SEQ ID NO: 10) and s70sR:ATA-gAAATAACCAgACgTAAgThT (SEQ ID NO: 11)) for 5 sec, and 60° C. for 4 min was performed. For nucleotide sequence analysis, ABI PRISM 310 GENETIC ANALYZER (Applied Biosystems) was used. Multiple alignment analysis was performed for the obtained nucleotide sequences using Clustal W computer program, and then phylogenetic trees were constructed by the neighbor-joining method (Mol. Biol. Evol. Vol. 4, No. 4,406-425) based on the genetic distance calculated with PHYLIP computer program package and Kimura's 2—parameter model (J. Mol. Evol. (1980) Vol. 16, No. 2, p. 111-20).

Figure 2:
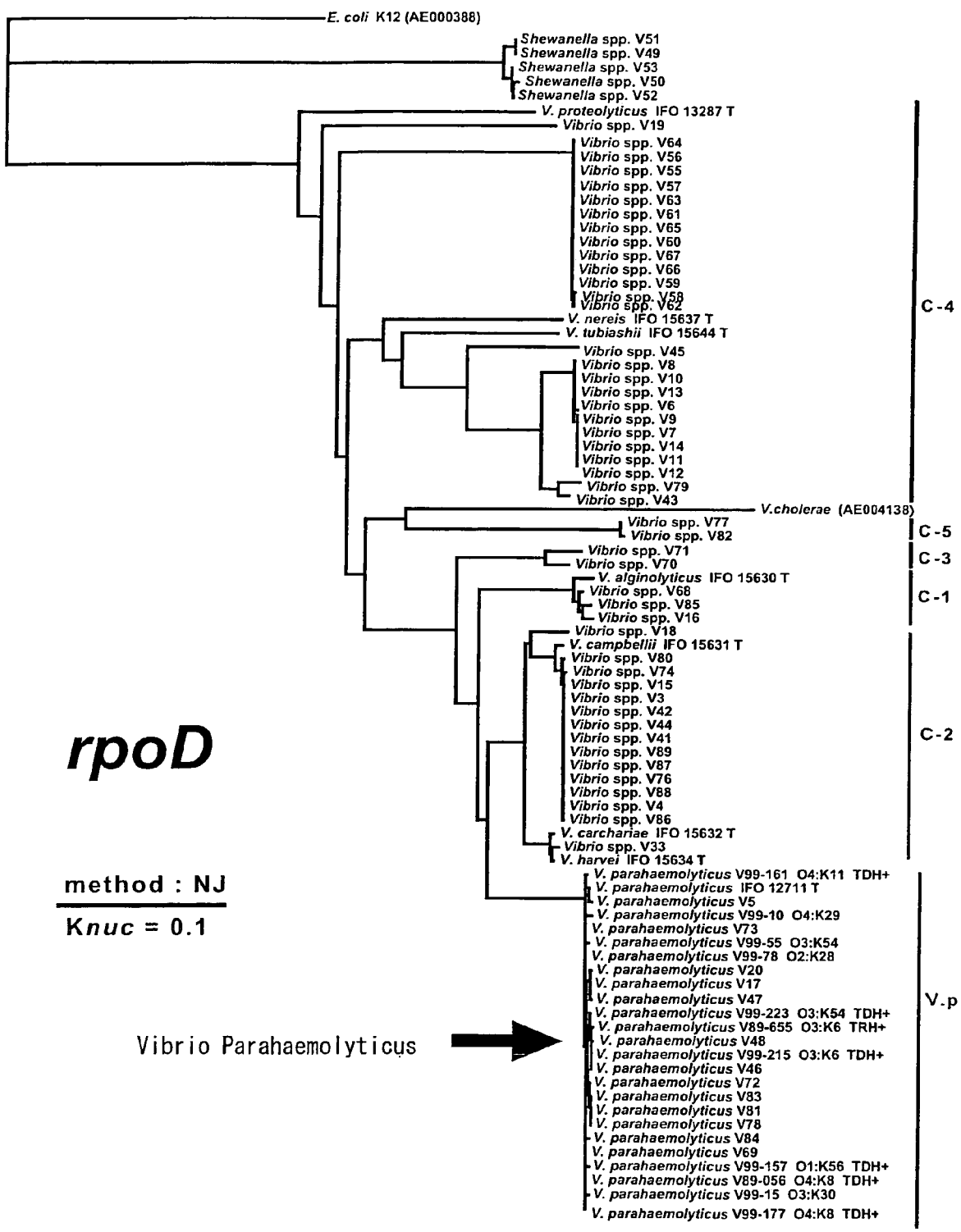
FIG. 2 Phylogenetic analysis of food-derived, *Vibrio parahaemolyticus*-like colonies based on rpoD gene Phylogenetic trees constructed by the neighbor-joining method (NJ) after analysis of an approximately 800 bp partial sequence of rpoD gene determined by direct sequencing method. Strains determined as *Vibrio parahaemolyticus* based on analysis of biochemical properties (the primary and secondary identification tests were performed according to the inspection guidelines for food hygiene) were described as *V. parahaemolyticus*. The phyletic group that *Vibrio parahameolyticus* belongs to is denoted as V. p, and other phyletic groups of the genus *Vibrio* are classified into C1 to 5 as shown in the figure. The rpoD gene sequence of *E. coli* strain K12 and that of *V. cholerae* used herein were accession Nos. AE000388 and AE004138 of the GenBank database.

As a result, it was shown that all the strains determined as *Vibrio parahaemolyticus* containing toxin genes (tdh or trh) and a type strain (IFO 12711 T) together compose an independent mono phyletic group, in the strains of the genus *Vibrio* (see FIG. 1). Therefore, it was suggested that constituents of bacteria belonging to this phylum should be determined as *Vibrio parahaemolyticus*. Next, for 64 strains which had been isolated from food samples and from *Vibrio parahaemolyticus*-like greenish blue colonies on TCBS agar media (NISSUI PHARIVIACEUTICAL CO., LTD), the nucleotide sequences of rpoD gene were determined by procedures similar to those used for the type strains, and then phylogenetic analysis was conducted. FIG. 2 shows the results. 11 out of 64 strains analyzed belonged to the phylum that should be determined as the above *Vibrio parahaemolyticus*. To verify the results of the gene analysis, biochemical properties were identified by performing examination according to the primary and secondary identification tests described in the guidelines for food inspection. Specifically, the primary identification test was performed for each of the parameters of oxidase, lactose/saccharose degradation ability using TSI media, gas generation ability upon glucose degradation, hydrogen sulfide production ability, indole production ability using SIM media, indole pyruvic acid production ability, confirmation of motility, lysine decarboxylase activity, Voges-Proskauer test and salt-tolerance (0, 3, 7 and 10% NaCl); the secondary identification test was performed for each of the parameters of ONPG, omithine decarboxylase activity, arginine dehydrase activity and fermentation ability for various sugars (arabinose, maltose, inosit, xylose, salicin, mannite, mannose, lactose and saccharose). In the primary identification test, *Vibrio parahaemolyticus* was shown to have the following properties; oxidase, positive; lactose/saccharose degradation in TSI media, no degradation; hydrogen sulfide, no production; gas generation upon glucose degradation, none; indole production ability on SIM media, positive; indolepyruvic acid production ability, negative; motility, positive; lysine decarboxylase activity, positive; Voges-Proskauer test, negative; and salt-tolerance (0, 3, 7 and 10% NaCl): −, +, + and −. In the secondary confirmation test, *Vibrio parahaemolyticus* was shown to have the following properties: ONPG, negative; omithine decarboxylase activity, positive; arginine dehydrase activity, negative; sugar fermentation ability (arabinose, positive; maltose, positive; inosit, negative; xylose, negative; salicin, negative; mannite, positive; mannose, positive; lactose, negative and saccharose, negative). The above biochemical examination revealed that only 11 strains which had been derived from food and belonged to the phylum that should be determined as *Vibrio parahaemolyticus* according to the previous analysis of rpoD gene were determined as *Vibrio parahaemolyticus*. Therefore, it was shown that *Vibrio parahaemolyticus* groups can be distinguished and identified accurately by analysis of rpoD gene.

To establish a genetic screening method capable of detecting only *Vibrio parahaemolyticus* constituents, the following procedures were performed. First, to clarify differences in nucleotide sequences among the closely related species, the nucleotide sequences of rpoD gene of the phylum that *Vibrio parahaemolyticus* belongs to and the neighbor phyla were compared, and then positions of nucleotides which are conserved among *Vibrio parahaemolyticus* constituents but differ from those of other bacteria belonging to the genus *Vibrio* were identified. Specifically, a consensus sequence of phyletic group that *Vibrio parahaemolyticus* belongs to was determined, while the consensus sequence was compared with those of the cluster C-1 to C-3, which are other pyletic groups of bacteria belonging to the genus *Vibrio* as shown by FIG. 2 to be phylogenetically close to the phylum that *Vibrio parahaemolyticus* belongs to. Thus, phylogenetically specific information was constructed (FIG. 3). It was shown that nucleotide positions 33, 93, 102, 123, 141, 147, 148, 192, 198, 204, 223, 229, 234, 243, 259, 261, 264, 267, 270, 384, 390, 501, 594, 597, 633, 712, 735 or 798 of SEQ ID NO: 1 in the Sequence Listing are characteristic in the phylum *Vibrio parahaemolyticus* belongs to. The use of a specific sequence of the this phylum containing these characteristic nucleotides enables the design of probes having high specificity and primers for gene amplification which have high specificity and excellent amplification efficiency.

For example, primers can be designed to always contain a position(s) at which a nucleotide(s) is different from that of closely related species, using the nucleotide sequence of rpoD gene comprising 15 or more consecutive nucleotides containing a nucleotide(s) different from that of the closely related species, preferably, 20 nucleotides or more, and further preferably, 20 nucleotides or more and 40 nucleotides or less. Similarly, probes can be designed to always contain a position(s) at which a nucleotide(s) is different from that of closely related species, using the nucleotide sequence of rpoD gene comprising 15 or more consecutive nucleotides containing a nucleotide(s) different from that of the closely related species, preferably, 20 nucleotides or more, and further preferably, 20 nucleotides or more and 100 nucleotides or less.

Further, regions that can be preferably used to prepare the primers and probes contain at a high frequency the above nucleotide(s) different from that of closely related species, for example, a region containing 259, 261, 264, 267 and 270; a region containing 141, 147 and 148; a region containing 192, 198 and 204: a region containing 223, 229 and 234; and a region containing 594 and 597. For primers, the 3' terminus is preferably a nucleotide specific to *Vibrio parahaemolyticus*.

The gene amplification primers of present inventions may be used for detecting, quantitatively determining or identifying *Vibrio parahaemolyticus*. The present invention encompasses a kit for detecting, quantitatively determining or identifying *Vibrio parahaemolyticus* which comprises these primers and probes and other reagents in combination.

TABLE 1

List of Strains Used

| | | | |
|---|---|---|---|
| Type strains of genus *Vibrio* | 8 strains | *V. parahaemolyticus* | IFO 12711 T |
| | | *V. alginolyticus* | IFO 15630 T |
| | | *V. proteolyticus* | IFO 13287 T |
| | | *V. nereis* | IFO 15637 T |
| | | *V. campbellii* | IFO 15631 T |

TABLE 1-continued

List of Strains Used

|  |  | V. harveyi | IFO 15634 T |  |
|---|---|---|---|---|
|  |  | V. carchariae | IFO 15632 T |  |
|  |  | V. tubiashii | IFO 15644 T |  |
| Stock Strains of | Derived from Human | V89-655 O3:K6 | TRH:+ |  |
| Vibrio parahaemolyticus | 13 strains | V89-056 O4:KB | TDH:+ |  |
|  |  | V99-157 O1:K56 | TDH:+ |  |
|  |  | V99-161 O4:K11 | TDH:+ |  |
|  |  | V99-177 O4:K8 | TDH:+ |  |
|  |  | V99-215 O3:K6 | TDH:+ |  |
|  |  | V99-223 O4:K9 | TDH:+ |  |
|  | Derived from Food | No toxin production: 6 strains |  |  |
| Isolated strains on TCBS media | 64 strains | Derived from food |  |  |
| Total | 85 strains |  |  |  |

EXAMPLES

The present invention will now be further described by means of examples. However, the examples represent embodiments of the present invention, and are not intended to limit the invention.

Specific detection of *Vibrio parahaemolyticus* was attempted by a PCR method using primers for detecting and identifying *Vibrio parahaemolyticus* shown in Table 2. In addition, primers described in Claims 10 to 15 are F1, F2, F5, F6, R1 and R2, respectively. Chromosome DNAs extracted from the test strains shown in Table 1 above were used as templates. Table 2 shows details about primers used. Amplification reaction was performed using thermostable DNA polymerase (AmpliTaq Gold: Applied Biosystems) and a GENE MATE thermal cycler (ISC BioExpress). A reaction solution was prepared to have a final volume of 20 µl and contain DNA 0.1 µg, 50 mM KCl, 10 mM Tris-HCl (pH 8.3), 1.5 mM MgCl$_2$, 0.01% gelatin, dNTP (0.2 mM each), 2.5 U of AmpliTaq Gold and primers (see Table 3 for concentration). A reaction condition consisted of activation with AmpliTaq Gold (95° C. for 10 min); 35 to 40 reaction cycles of 94° C. for 1 min, annealing for 1 min (see Table 3 for temperature), and 72° C. for 1 min; and then elongation reaction at 72° C. for 10 min was performed. Table 3 shows primer combinations and amplification reaction conditions. 5 µl of the reaction solution after amplification was subjected to 2% agarose gel (agarose S: NIPPON GENE CO., LTD.) electrophoresis (0.5×TAE, 100V for 30 min), and then stained with ethidium bromide for 10 min, followed by confirmation of the presence or absence of amplified rpoD genes under ultraviolet radiation.

Using 4 types of sense primers and 2 types of antisense primers, that is, 8 combinations of primers in total, DNAs of the test strains were screened. Thus, only the DNAs belonging to the phylum that should be determined as *Vibrio parahaemolyticus* were positive (Table 4).

TABLE 2

Primers for specific detection of *Vibrio parahaemolyticus*

|  | Primer | Sequence | Length | Position[a] | Direction |
|---|---|---|---|---|---|
| SEQ. ID. NO: 3 | F1 | agarcttcgtctgactgatt | 20 | 129–148 | Sense |
| SEQ. ID. NO: 4 | F2 | aagaagacctagaagatgat | 20 | 251–270 | Sense |
| SEQ. ID. NO: 5 | F5 | cagcwgcgccaaccgcgact | 20 | 185–204 | Sense |
| SEQ. ID. NO: 6 | F6 | ctgarctgtctgaarctcaa | 20 | 215–234 | Sense |
| SEQ. ID. NO: 7 | R1 | gttaccagtgaatagggca | 19 | 609–591 | Antisense |
| SEQ. ID. NO: 8 | R2 | attcgttaccagtgaatagg | 20 | 613–594 | Antisense |

[a]indicates a position from the 5' terminus in the nucleotide sequence represented by SEQ

TABLE 3

PCR conditions for primers for specific detection of *Vibrio parahaemolyticus*

| | | PCR conditions | | | |
|---|---|---|---|---|---|
| Sense primer | Antisense primer | Amplified product (bp) | Annealing temperature (° C.) | Number of cycles | Primer concentration (mM) |
| F1 | R1 | 483 | 58 | 35 | 0.1 |
| F2 | R1 | 361 | 56 | 40 | 0.1 |
| F5 | R1 | 427 | 64 | 40 | 0.1 |
| F6 | R1 | 397 | 60 | 35 | 0.1 |
| F1 | R2 | 485 | 58 | 40 | 0.1 |
| F2 | R2 | 365 | 60 | 40 | 0.5 |
| F5 | R2 | 431 | 60 | 40 | 0.1 |
| F6 | R2 | 401 | 56 | 40 | 0.1 |

TABLE 4

PCR result using primers for specific detection of *Vibrio parahaemolyticus*

| Cluster | Name | Strain name | Kanagawa phenomenon | PCR | | | | | | | |
|---|---|---|---|---|---|---|---|---|---|---|---|
| | | | | F1 & R1 | F2 & R1 | F5 & R1 | F6 & R1 | F1 & R2 | F2 & R2 | F5 & R2 | F6 & R2 |
| V. p | *V. parahaemolyticus* | V99-161 | + | + | + | + | + | + | + | + | + |
| V. p | *V. parahaemolyticus* | IFO 12711 T | − | + | + | + | + | + | + | + | + |
| V. p | *V. parahaemolyticus* | V5 | − | + | + | + | + | + | + | + | + |
| V. p | *V. parahaemolyticus* | V99-10 | − | + | + | + | + | + | + | + | + |
| V. p | *V. parahaemolyticus* | V73 | − | + | + | + | + | + | + | + | + |
| V. p | *V. parahaemolyticus* | V99-55 | − | + | + | + | + | + | + | + | + |
| V. p | *V. parahaemolyticus* | V99-78 | − | + | + | + | + | + | + | + | + |
| V. p | *V. parahaemolyticus* | V20 | − | + | + | + | + | + | + | + | + |
| V. p | *V. parahaemolyticus* | V17 | − | + | + | + | + | + | + | + | + |
| V. p | *V. parahaemolyticus* | V47 | − | + | + | + | + | + | + | + | + |
| V. p | *V. parahaemolyticus* | V99-223 | + | + | + | + | + | + | + | + | + |
| V. p | *V. parahaemolyticus* | V89-655 | − | + | + | + | + | + | + | + | + |
| V. p | *V. parahaemolyticus* | V48 | − | + | + | + | + | + | + | + | + |
| V. p | *V. parahaemolyticus* | V99-215 | + | + | + | + | + | + | + | + | + |
| V. p | *V. parahaemolyticus* | V46 | − | + | + | + | + | + | + | + | + |
| V. p | *V. parahaemolyticus* | V72 | − | + | + | + | + | + | + | + | + |
| V. p | *V. parahaemolyticus* | V83 | − | + | + | + | + | + | + | + | + |
| V. p | *V. parahaemolyticus* | V81 | − | + | + | + | + | + | + | + | + |
| V. p | *V. parahaemolyticus* | V78 | − | + | + | + | + | + | + | + | + |
| V. p | *V. parahaemolyticus* | V84 | − | + | + | + | + | + | + | + | + |
| V. p | *V. parahaemolyticus* | V69 | − | + | + | + | + | + | + | + | + |
| V. p | *V. parahaemolyticus* | V99-157 | + | + | + | + | + | + | + | + | + |
| V. p | *V. parahaemolyticus* | V89-056 | + | + | + | + | + | + | + | + | + |
| V. p | *V. parahaemolyticus* | V99-15 | | + | + | + | + | + | + | + | + |
| V. p | *V. parahaemolyticus* | V99-177 | + | + | + | + | + | + | + | + | + |
| C-2 | *V. harveyi* | IFO 15634 T | − | − | − | − | − | − | − | − | − |
| C-2 | *Vibrio* spp. | V33 | − | − | − | − | − | − | − | − | − |
| C-2 | *V. carchariae* | IFO 15632 T | − | − | − | − | − | − | − | − | − |
| C-2 | *Vibrio* spp. | V80 | − | − | − | − | − | − | − | − | − |
| C-2 | *Vibrio* spp. | V74 | − | − | − | − | − | − | − | − | − |
| C-2 | *Vibrio* spp. | V15 | − | − | − | − | − | − | − | − | − |
| C-2 | *Vibrio* spp. | V3 | − | − | − | − | − | − | − | − | − |
| C-2 | *Vibrio* spp. | V42 | − | − | − | − | − | − | − | − | − |
| C-2 | *Vibrio* spp. | V44 | − | − | − | − | − | − | − | − | − |
| C-2 | *Vibrio* spp. | V41 | − | − | − | − | − | − | − | − | − |
| C-2 | *Vibrio* spp. | V89 | − | − | − | − | − | − | − | − | − |
| C-2 | *Vibrio* spp. | V87 | − | − | − | − | − | − | − | − | − |
| C-2 | *Vibrio* spp. | V76 | − | − | − | − | − | − | − | − | − |
| C-2 | *Vibrio* spp. | V88 | − | − | − | − | − | − | − | − | − |
| C-2 | *Vibrio* spp. | V4 | − | − | − | − | − | − | − | − | − |
| C-2 | *Vibrio* spp. | V86 | − | − | − | − | − | − | − | − | − |
| C-2 | *V. campbelli* | IFO 15631 T | − | − | − | − | − | − | − | − | − |
| C-2 | *Vibrio* spp. | V18 | − | − | − | − | − | − | − | − | − |
| C-1 | *Vibrio* spp. | V68 | − | − | − | − | − | − | − | − | − |
| C-1 | *Vibrio* spp. | V85 | − | − | − | − | − | − | − | − | − |
| C-1 | *Vibrio* spp. | V16 | − | − | − | − | − | − | − | − | − |
| C-1 | *V. alginolyticus* | IFO 15630 T | − | − | − | − | − | − | − | − | − |
| C-3 | *Vibrio* spp. | V70 | − | − | − | − | − | − | − | − | − |
| C-3 | *Vibrio* spp. | V71 | − | − | − | − | − | − | − | − | − |
| C-5 | *Vibrio* spp. | V77 | − | − | − | − | − | − | − | − | − |
| C-5 | *Vibrio* spp. | V82 | − | − | − | − | − | − | − | − | − |
| C-4 | *Vibrio* spp. | V45 | − | − | − | − | − | − | − | − | − |
| C-4 | *Vibrio* spp. | V8 | − | − | − | − | − | − | − | − | − |
| C-4 | *Vibrio* spp. | V10 | − | − | − | − | − | − | − | − | − |
| C-4 | *Vibrio* spp. | V13 | − | − | − | − | − | − | − | − | − |
| C-4 | *Vibrio* spp. | V6 | − | − | − | − | − | − | − | − | − |
| C-4 | *Vibrio* spp. | V9 | − | − | − | − | − | − | − | − | − |
| C-4 | *Vibrio* spp. | V7 | − | − | − | − | − | − | − | − | − |
| C-4 | *Vibrio* spp. | V14 | − | − | − | − | − | − | − | − | − |
| C-4 | *Vibrio* spp. | V11 | − | − | − | − | − | − | − | − | − |
| C-4 | *Vibrio* spp. | V12 | − | − | − | − | − | − | − | − | − |
| C-4 | *Vibrio* spp. | V79 | − | − | − | − | − | − | − | − | − |
| C-4 | *Vibrio* spp. | V43 | − | − | − | − | − | − | − | − | − |
| C-4 | *V. tubiashii* | IFO 15644 T | − | − | − | − | − | − | − | − | − |
| C-4 | *V. nereis* | IFO 15637 T | − | − | − | − | − | − | − | − | − |
| C-4 | *Vibrio* spp. | V64 | − | − | − | − | − | − | − | − | − |
| C-4 | *Vibrio* spp. | V56 | − | − | − | − | − | − | − | − | − |
| C-4 | *Vibrio* spp. | V55 | − | − | − | − | − | − | − | − | − |
| C-4 | *Vibrio* spp. | V57 | − | − | − | − | − | − | − | − | − |
| C-4 | *Vibrio* spp. | V63 | − | − | − | − | − | − | − | − | − |
| C-4 | *Vibrio* spp. | V61 | − | − | − | − | − | − | − | − | − |
| C-4 | *Vibrio* spp. | V65 | − | − | − | − | − | − | − | − | − |

TABLE 4-continued

PCR result using primers for specific detection of *Vibrio parahaemolyticus*

| Cluster | Name | Strain name | Kanagawa phenomenon | F1 & R1 | F2 & R1 | F5 & R1 | F6 & R1 | F1 & R2 | F2 & R2 | F5 & R2 | F6 & R2 |
|---------|------|-------------|---------------------|---------|---------|---------|---------|---------|---------|---------|---------|
| C-4 | *Vibrio* spp. | V60 | − | − | − | − | − | − | − | − | − |
| C-4 | *Vibrio* spp. | V67 | − | − | − | − | − | − | − | − | − |
| C-4 | *Vibrio* spp. | V66 | − | − | − | − | − | − | − | − | − |
| C-4 | *Vibrio* spp. | V59 | − | − | − | − | − | − | − | − | − |
| C-4 | *Vibrio* spp. | V58 | − | − | − | − | − | − | − | − | − |
| C-4 | *Vibrio* spp. | V62 | − | − | − | − | − | − | − | − | − |
| C-4 | *Vibrio* spp. | V19 | − | − | − | − | − | − | − | − | − |
| C-4 | *V. proteolyticus* | IFO 13287 T | − | − | − | − | − | − | − | − | − |
|  | *Shewanella* spp. | V51 | − | − | − | − | − | − | − | − | − |
|  | *Shewanella* spp. | V49 | − | − | − | − | − | − | − | − | − |
|  | *Shewanella* spp. | V53 | − | − | − | − | − | − | − | − | − |
|  | *Shewanella* spp. | V50 | − | − | − | − | − | − | − | − | − |
|  | *Shewanella* spp. | V52 | − | − | − | − | − | − | − | − | − |

INDUSTRIAL APPLICABILITY

The rpoD gene primers and probes of the present invention are excellent in terms of detection accuracy because they have been designed based on a thorough understanding of the phylogenetic relation with *Vibrio parahaemolyticus*, by which improvement of the specificity has been studied. Therefore, the rpoD gene primers and probes are of great advantage for direct detection under conditions where bacteria are not isolated from food, and allied bacterial species exist together.

Free Text in Sequence Listing

SEQ ID Nos. 9-12 are primers.

Present specification incorporates by reference contents of specification including claims and drawings of patent application number 2001-235806 filed in the Japan Patent Office on Aug. 3, 2001 on which priority is claimed.

The invention claimed is:

1. A polynucleotide fragment consisting of from 15 to 100 nucleotides of SEQ ID NO: 1, or the complementary strand of said fragment, wherein said polynucleotide fragment contains at least one nucleotide position that is conserved among *Vibrio parahaemolyticus* strains, and which differs in other bacteria of the genus *Vibrio*, said nucleotide position being selected from the group consisting of nucleotide position Nos. 33, 93, 102, 123, 141, 147, 148, 192, 198, 204, 223, 229, 234, 243, 259, 261, 264, 267, 270, 384, 390, 501, 594, 597, 633, 712, 735 and 798 of SEQ ID NO: 1.

2. The polynucleotide fragment or complementary strand thereof of claim 1, wherein said fragment contains position Nos. 259, 261, 264, 267 and 270 of SEQ ID NO: 1.

3. The polynucleotide fragment or complementary strand thereof of claim 1, wherein said fragment contains position Nos. 141, 147 and 148 of SEQ ID NO: 1.

4. The polynucleotide fragment or complementary strand thereof of claim 1, wherein said fragment contains position Nos. 192, 198 and 204 of SEQ ID NO: 1.

5. The polynucleotide fragment or complementary strand thereof of claim 1, wherein said fragment contains position Nos. 223, 229 and 234 of SEQ ID NO: 1.

6. The polynucleotide fragment or complementary strand thereof of claim 1, wherein said fragment contains position Nos. 594 and 597 of SEQ ID NO: 1.

7. The polynucleotide fragment or complementary strand thereof of claim 1, wherein the nucleotide at the 3' terminus of said fragment is selected from the group consisting of nucleotide position No. 33, 93, 102, 123, 141, 147, 148, 192, 198, 204, 223, 229, 234, 243, 259, 261, 264, 267, 270, 384, 390, 501, 594, 597, 633, 712, 735 and 798 of SEQ ID NO: 1.

8. The polynucleotide fragment or complementary strand thereof of claim 1, wherein said fragment comprises SEQ ID NO: 3.

9. The polynucleotide fragment or complementary strand thereof of claim 1, wherein said fragment comprises SEQ ID NO: 4.

10. The polynucleotide fragment or complementary strand thereof of claim 1, wherein said fragment comprises SEQ ID NO: 5.

11. The polynucleotide fragment or complementary strand thereof of claim 1, wherein said fragment comprises SEQ ID NO:6.

12. The polynucleotide fragment or complementary strand thereof of claim 1, wherein said fragment comprises SEQ ID NO: 7.

13. The polynucleotide fragment or complementary strand thereof of claim 1, wherein said fragment comprises SEQ ID NO: 8.

14. A method for detecting, quantitatively determining or identifying *Vibrio parahaemolyticus*, comprising, using the polynucleotide fragment or complementary strand thereof of claim 1 as a primer in a PCR reaction.

15. A kit comprising two or more polynucleotide fragments or complementary strands thereof of claim 1.

16. The polynucleotide fragment or complementary strand thereof of claim 1, wherein said fragment consists of from 20 to 100 nucleotides of SEQ ID NO:1.

17. The polynucleotide fragment or complementary strand thereof of claim 1, wherein said fragment consists of from 20 to 40 nucleotides of SEQ ID NO: 1.

* * * * *

SEQUENCE LISTING

<160> NUMBER OF SEQ ID NOS: 12

<210> SEQ ID NO 1
<211> LENGTH: 807
<212> TYPE: DNA
<213> ORGANISM: Vibrio parahaemolyticus

<400> SEQUENCE: 1

```
actcgcraag gcgaaatcga catcgcaaaa cgcattgaag aaggtattaa ccaagttcaa      60
tcgtctgttg ctgaatacco tggcactatt ccttacatcc tagagcaatt tgataargtt     120
caggcagaag arcttcgtct gactgattta atctctggct ttgtagatcc tgacgctgac     180
gatacagcwg cgccaaccgc gactcacatc ggttctgarc tgtctgaarc tcaattagaa     240
gaggaagacg aagaagacct agaagatgat gaagaragcg atgacgattc agatgaytcr     300
gaagaagatg taggtattga yccagagctr gcgcttgaga aattcaacca gctacgcagc     360
acataccaaa atcttcagct agcgatcaat gagtacggct acgacagccc gaaagcaacc     420
gttgctaacg aaatgatgct rgacgtattc aaagaattcc gtctaacacc aaaacagttc     480
gaccacctag tgaacgaact tcgyacwgca atggatcgcg ttcgtactca agaacgtttg     540
atcatgaagt ctgtggttga atacggcaaa atgccgaaga aatcgttyat tgccctattc     600
actggtaacg aatcaagtga tgcatggcta gacgagatcc tmgcatctga caagccatac     660
gctgagaaaa tcaaacgtaa cgaagaagag atccgtcgtt caatckckaa gttaaaaatg     720
attgaagaag agacatmtct aaacgtacar aacattaaag acatcagccg tcgcatgtct     780
```

-continued

```
atcggtgaag cgaaagcacg ccgtgcg                                         807

<210> SEQ ID NO 2
<211> LENGTH: 807
<212> TYPE: DNA
<213> ORGANISM: Artificial Sequence
<220> FEATURE:
<223> OTHER INFORMATION: Description of Artificial Sequence:
      Consensus sequence among
      Vibrio spp. other than Vibrio haemolyticus
<220> FEATURE:
<221> NAME/KEY: modified_base
<222> LOCATION: (507)
<223> OTHER INFORMATION: a, t, c or g
<220> FEATURE:
<221> NAME/KEY: modified_base
<222> LOCATION: (555)
<223> OTHER INFORMATION: a, t, c or g

<400> SEQUENCE: 2
actcgcgaag gcgaaatcga catcgcaaaa cgtattgaag aaggtattaa ccaagttcaa      60
tcgtctgttg ctgaataccc wggyacdaty ccrtacatyc ttgagcartt tgayaargtw     120
caagcwgaag aaytdcgtct wacwgacctw atytcwgght ttgthgaycc wgaygchgay     180
gayacvrcwg chccracrgc racrcacaty ggttctgarc tractgaatc tcagytagaa     240
gawgaagayg awgaagacgt tgatgamgac gaagawrgyg aygayrrykm wgatgahdcw     300
gargaagatg twggtatyga yccwgarytd gcgctwgaga aattcaacca rctacgcagy     360
acvtaycaaa aycttcaryt wgcaatcaac garyacggyt ayravagycc kaaagcracm     420
gtwgcwaayg arwtgatgct agacgtatty mrmgarttyc gtctracrcc waaacagtty     480
gaycacytag traaygaayt rcgyacnkcd atggatcgyg ttcgtacwca agarcgyytg     540
atcatgaark cwryngttga atacggcaaa atgccgaaga aatcrttyat ygcrctgtty     600
acwggyaayg aatcwashga wgcwtggytr gatgarrtyy twkcwtcwga yaagccatac     660
gctgaraara tyaaacgtar cgaagaagar atycgycgyt caatcrctaa rctaaaratg     720
attgarrahg aracytmtct rammgtwcar aacatyaaag acatcagccg tcgyatgtmt     780
atcggtgaag craaagmkcg ycgtgck                                         807

<210> SEQ ID NO 3
<211> LENGTH: 20
<212> TYPE: DNA
<213> ORGANISM: Vibrio parahaemolyticus

<400> SEQUENCE: 3
agarcttcgt ctgactgatt                                                  20

<210> SEQ ID NO 4
<211> LENGTH: 20
<212> TYPE: DNA
<213> ORGANISM: Vibrio parahaemolyticus

<400> SEQUENCE: 4
aagaagacct agaagatgat                                                  20

<210> SEQ ID NO 5
<211> LENGTH: 20
<212> TYPE: DNA
<213> ORGANISM: Vibrio parahaemolyticus

<400> SEQUENCE: 5
cagcwgcgcc aaccgcgact                                                  20
```

<210> SEQ ID NO 6
<211> LENGTH: 20
<212> TYPE: DNA
<213> ORGANISM: Vibrio parahaemolyticus

<400> SEQUENCE: 6
ctgarctgtc tgaarctcaa                                                    20

<210> SEQ ID NO 7
<211> LENGTH: 19
<212> TYPE: DNA
<213> ORGANISM: Vibrio parahaemolyticus

<400> SEQUENCE: 7
gttaccagtg aatagggca                                                     19

<210> SEQ ID NO 8
<211> LENGTH: 20
<212> TYPE: DNA
<213> ORGANISM: Vibrio parahaemolyticus

<400> SEQUENCE: 8
attcgttacc agtgaatagg                                                    20

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (30)
<223> OTHER INFORMATION: a, t, c or g
<220> FEATURE:
<221> NAME/KEY: modified_base
<222> LOCATION: (39)
<223> OTHER INFORMATION: a, t, c or g
<220> FEATURE:
<221> NAME/KEY: modified_base
<222> LOCATION: (42)
<223> OTHER INFORMATION: a, t, c or g

<400> SEQUENCE: 9
acgactgacc cggtacgcat gtayatgmgn garatgggna cngt                         44

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 10
acgactgacc cggtacgcat gta                                                23

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (24)
<223> OTHER INFORMATION: a, t, c or g
<220> FEATURE:

-continued

```
<221> NAME/KEY: modified_base
<222> LOCATION: (30)
<223> OTHER INFORMATION: a, t, c or g

<400> SEQUENCE: 11
atagaaataa ccagacgtaa gttngcytcn accatytcyt tytt                     44

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 12
atagaaataa ccagacgtaa gtt                                            23
```